US 12,274,450 B2

(12) United States Patent
Pile-Spellman et al.

(10) Patent No.: US 12,274,450 B2
(45) Date of Patent: Apr. 15, 2025

(54) DEVICES AND METHODS FOR TRANS-ARTERIAL OSMOTIC EMBOLIZATION OF PATHOLOGICAL TISSUE

(71) Applicant: Transluminal Systems, LLC, New Rochelle, NY (US)

(72) Inventors: John Pile-Spellman, Pelham, NY (US); Jae H. Choi, Mineola, NY (US)

(73) Assignee: Transluminal Systems, LLC, New Rochelle, NY (US)

( * ) Notice: Subject to any disclaimer, the term of this patent is extended or adjusted under 35 U.S.C. 154(b) by 620 days.

(21) Appl. No.: 17/391,136

(22) Filed: Aug. 2, 2021

(65) Prior Publication Data

US 2022/0031336 A1 Feb. 3, 2022

Related U.S. Application Data

(60) Provisional application No. 63/060,197, filed on Aug. 3, 2020.

(51) Int. Cl.
| | |
|---|---|
| *A61B 17/12* | (2006.01) |
| *A61B 6/00* | (2024.01) |
| *A61B 6/50* | (2024.01) |
| *A61M 5/00* | (2006.01) |
| *A61B 17/00* | (2006.01) |

(52) U.S. Cl.
CPC ........ *A61B 17/12186* (2013.01); *A61B 6/504* (2013.01); *A61M 5/007* (2013.01); *A61B 2017/00022* (2013.01); *A61B 2017/1205* (2013.01); *A61M 2205/3327* (2013.01); *A61M 2205/3334* (2013.01)

(58) Field of Classification Search
CPC .............. A61B 17/12186; A61B 6/504; A61B 2017/00022; A61B 2017/1205; A61B 5/055; A61B 17/1204; A61M 5/007; A61K 41/0038; A61K 47/26
See application file for complete search history.

(56) References Cited

U.S. PATENT DOCUMENTS

| | | | |
|---|---|---|---|
| 8,824,752 B1 * | 9/2014 | Fonte ..................... | A61B 6/481 |
| | | | 382/126 |
| 2004/0167415 A1 * | 8/2004 | Gelfand ........... | A61B 17/12109 |
| | | | 600/500 |

(Continued)

*Primary Examiner* — Baisakhi Roy
(74) *Attorney, Agent, or Firm* — Nikitas E. Nicolakis; Lombard & Geliebter LLP

(57) ABSTRACT

An endovascular interventional method is provided that includes the steps of: inserting a catheter into a target blood vessel, wherein the catheter is coupled to a system that provides a continuous delivery of contrast and of a hyperosmotic fluid supply; injecting the contrast and determining a rate of flow that achieves angiographic filling of the target blood vessel at a first time; injecting the hyperosmotic fluid continuously at the rate of flow that achieves angiographic filling at the first time for a first period of time; injecting the contrast and determining a rate of flow that achieves angiographic filling of the target blood vessel at a second time following the first period of time; and injecting the hyperosmotic fluid continuously at the rate of flow that achieves angiographic filling at the second time for a second period of time.

20 Claims, 2 Drawing Sheets

(56) References Cited

U.S. PATENT DOCUMENTS

| | | | | |
|---|---|---|---|---|
| 2005/0261726 A1* | 11/2005 | Pile-Spellman | ... | A61B 17/1204 606/200 |
| 2005/0265923 A1* | 12/2005 | Toner | ................ | A61K 41/0038 424/1.11 |
| 2006/0204443 A1* | 9/2006 | Kobayashi | ........... | A61K 49/124 600/1 |
| 2007/0135343 A1* | 6/2007 | Webb | ....................... | A61K 9/19 514/14.2 |
| 2012/0243761 A1* | 9/2012 | Senzig | ................ | A61B 6/5217 378/19 |
| 2013/0211247 A1* | 8/2013 | Kalafut | ................ | A61B 6/507 703/11 |
| 2015/0057538 A1* | 2/2015 | Cragg | ................... | A61M 5/007 600/431 |
| 2017/0079581 A1* | 3/2017 | Walczak | ................ | A61K 47/26 |
| 2019/0117179 A1* | 4/2019 | Goyal | ..................... | A61B 6/463 |
| 2019/0350486 A1* | 11/2019 | Walczak | ................ | A61B 5/055 |
| 2020/0078602 A1* | 3/2020 | Hirsh | ..................... | A61N 5/103 |
| 2020/0245961 A1* | 8/2020 | Butler | ................... | A61B 6/5258 |
| 2021/0334963 A1* | 10/2021 | Isgum | .................... | G16H 50/20 |

* cited by examiner

| | OSMOTIC EMBOLIZATION | PARTICLE-LIQUID EMBOLIZATION | CHEMO EMBOLIZATION | RADIO EMBOLIZATION |
|---|---|---|---|---|
| Deep Watershed Penetration For More Complete And Definitive Embolization Of Target Tissue | yes | no | no | no |
| Instant & Permanent Target Tissue Shrinkage | yes | no | no | no |
| Treatment Of Target Tissue Edema And Reduction of Mass Effect | yes | no | no | no |
| Tolerant for Inadvertent Off-Target Arterial Embolization That May Cause Ischemic Damage To Normal Tissue | yes | no | no | no |
| Tolerant for Inadvertent Venous Embolization That May Cause Hemorrhage And Normal Tissue Damage | yes | no | yes | yes |
| Tolerant for Fluoroscopic Challenges And Poor Visualization | yes | no | no | no |
| Dose Dependent, Well-Established Range For Concentration Threshold For Tissue | yes | no | no | yes |
| Non-IschemicMummification of Target Tissue | yes | no | no | no |
| Additional Non-Ischemic Cytotoxic Effects on Cellular Proteins and DNA | yes | no | yes | yes |
| Low Cost Embolic Agent | yes | no | no | no |
| | | | | |
| Painless | no | yes | yes | yes |
| Pharmacopedia & Device Supported | no | yes | yes | yes |

Table 1. Embolic Agents: Osmotic vs Others

Fig. 3

DEVICES AND METHODS FOR TRANS-ARTERIAL OSMOTIC EMBOLIZATION OF PATHOLOGICAL TISSUE

BACKGROUND

The present application relates to methods and devices/systems for the embolization of pathologic tissue.

Arterial embolization is routine for the treatment of pathologic lesions, such as tumors, and vascular malformations, such as arterio-venous malformations. This routine embolization is performed by placing a catheter under X-ray guidance into the target vessel. Radiographic contrast is then injected, and an angiogram is performed. A smaller catheter may be placed distally in the target vessel and additional images of the area of interest obtained. Under X-ray control, the embolic agent in injected which is carried to the tissue by the blood flow.

Immediate post-embolization swelling or hemorrhage are found frequently with routine embolization. Additionally, inadvertent embolization with particles or solidifying liquid agents of adjacent feeding collaterals to normal tissue is problematic. Sometimes, these feeding collaterals are poorly visualized due to overlaying bone and moving soft tissue, such as the bowel, which is problematic when, for instance, the lesion to be embolized is located along the spine.

With routine embolizing agents, such as PVA or Embospheres™, as well as liquid agents, such as Onyx™ and Truefill™, post-embolization cytotoxic and vasogenic edema or hemorrhage occur frequently and can cause damage to critical tissue adjacent to the lesion to be embolized. Additionally, a complete devascularization with routine embolizing agents is often difficult in hypervascular tumors that feature both branching and non-branching angiogenesis due to incomplete penetration. Also, proximal occlusions at the pre-capillary level often fail to totally devascularize the tumor, leading to "islands" of residual tumor. Chemo-therapeutic embolic and radioactive embolic agents partly address the heterogeneous penetration problem of routine particles or liquids, but do not devascularize the tumor acutely.

These methods often leave untreated a 'rim' of a tumor, frustrating attempts at definitive cure. This is based on incomplete penetration of the embolic agent into the presumed vascular territory. In these methods, a catheter is placed into the targeted vessel, which markedly decreases the luminal diameter, which in turn, decreases the blood pressure therein, which in turn decreases the 'effective vascular territory'. Vascular territories are dynamic, and in the case where one vessel is narrowed, it gives up its distal territory to its adjacent neighbors. This phenomenon is referred to as a 'watershed shift'. This 'shift' can happen immediately and can cause a complete 'kidnapping" of the vascular territory by its neighbors. Unfortunately, this is common in tumor embolization, and leads often to a "rim" of untreated viable tissue at the edge of the embolized vascular territory.

At the vascular-tissue unit level, routine embolization is binary—similar in some ways to 'bullets'—and embolization is done by repeatedly 'shooting' the embolic material into the target lesion under X-ray guidance. After a number of these 'bullets', the flow to the lesion slows down. Smaller and less frequent bullets are used until there is arrest of the forward flow. The embolic material is opacified by contrast, but seeing small amounts of contrast can be challenging, requiring significant expertise and specialized materials to perform the process effectively. Reflux into non-target vascular territories can let these 'bullets' be carried quite far by the blood stream and cause unintended damage to normal tissue or even death. The complications of 'off-target' emboli are well documented. Additionally, liquid agents and small particles can lodge in the draining veins, especially in tissues that have significant arterio-venous shunts. Occlusion of the draining veins is associated with swelling and bleeding.

Additionally, this type of embolization requires extremely high-fidelity X-ray imaging with excellent spatial and temporal resolution with real time image processing capabilities, digital subtraction angiography, and must be powerful enough to penetrate dense body parts. Even when using technically advanced machines, the procedure can easily be frustrated by tiny patient movements.

In summary, routine tumor embolization is technically challenging, requires the most advanced equipment, rarely leads to complete cure of the targeted lesion, and carries a significant risk for serious complications. Thus, it has found limited acceptance in the medical community, being used as a last resort palliative maneuver, or as an adjunct prior to surgery for hypervascular lesions. Accordingly, there is a need for methods and devices/systems for embolizing tissue that are not so limited.

SUMMARY

The present application provides methods and devices/systems for osmotic embolization of tissue, which addresses one or more of these difficulties in the art for tumor embolization. Unlike the prior methods where embolization of the target vasculature with embolic materials is the key feature, osmotic embolization dehydrates the target tissue. Benefits of osmotic embolization over other form of embolization are outlined in FIG. 3 (Table 1) appended hereto.

Generally, osmotic embolization may begin with a micro catheter being placed in the target tissue artery to perform super-selective angiography. Contrast may then be injected, and the rate that leads to complete opacification of the vessel with little reflux is noted. The osmotic embolic agent is then injected at this rate and pressure. Intermittently, contrast is injected and the flow rate of the osmotic embolic agent adjusted to the rate that completely opacifies the vessel, with minimal reflux. Initially, the osmotic embolic agent may cause marked vasodilation, requiring an increase in the injection rate of the osmotic embolic agent. After a few minutes, the flow in the target vessel slows, and finally, essentially stops. The smaller conduit vessels (<0.5 mm) can be seen. At this time, if appropriate, the proximal feeding artery can be occluded with a coil or some other agent.

The present application provides new devices/systems to facilitate osmotic embolization, as disclosed herein. Osmotic embolization kills the tissue by removing a certain percentage of the water from the cells. This is preferably done with a continuous uninterrupted high osmotic infusion until terminal dehydration occurs. Pausing for any reason may allow the tissues to quickly rehydrate and will result in an ineffective outcome.

Inadvertent reflux of the osmotic embolic liquid is not believed to be problematic. The refluxed material will quickly become diluted, with the off-site target tissues never reaching an osmotic gradient large enough for terminal dehydration. For this reason, the embolization can be done with intermittent fluoroscopic confirmation. The initial vasodilation allows deep penetration into the far watershed regions of the lesion, making residual "rims" of untreated tissue less likely. As a liquid, the agent penetrates all aspects of the tissue without any viable tumor 'islands' left to regrow. The dehydration reduces the volume of the tissue by an estimated 10-40%, with associated reduction in local mass effect. Osmotic stress is known to destroy proteins, macro-molecules, as well as DNA, and increases the damage due to oxidative stress. Osmotic agents may be painful and at present, there are no devices and methods suitable for their routine use.

Present devices in the art make continuous uninterrupted high flow for extended periods, with intermittent visualization with contrast, extremely difficult to obtain. The disclosure of the methods and devices herein overcome such issues.

In one aspect, an endovascular interventional method is provided that includes the steps of: inserting a catheter into a target blood vessel, wherein the catheter is coupled to a system that provides a continuous delivery of contrast and of a hyperosmotic fluid supply; injecting the contrast and determining a rate of flow that achieves angiographic filling of the target blood vessel at a first time; injecting the hyperosmotic fluid continuously at the rate of flow that achieves angiographic filling at the first time for a first period of time; injecting the contrast and determining a rate of flow that achieves angiographic filling of the target blood vessel at a second time following the first period of time; and injecting the hyperosmotic fluid continuously at the rate of flow that achieves angiographic filling at the second time for a second period of time.

In one embodiment, the hyperosmotic fluid comprises an osmotic embolic agent.

In one embodiment, the first and second periods of time are about 20 minutes to about 30 minutes.

In one embodiment, the includes repeating the steps of injecting contrast and the hyperosmotic fluid until the flow rate at the second time is reduced.

In one embodiment, the includes repeating the steps of injecting contrast and the hyperosmotic fluid until the flow rate at the second time is reduced to a negligible flow rate.

In one embodiment, the includes repeating the steps of injecting contrast and the hyperosmotic fluid until the flow rate at the second time signals completion of osmotic embolization at the target vessel.

In one embodiment, the flow of the contrast is off when flow of the hyperosmotic fluid is turned on.

In one embodiment, the flow of the hyperosmotic fluid is off when flow of the contrast is turned on.

In one embodiment, the system comprises at least one sensor for determining flow rate and wherein the first and second flow rates are determined based on feedback from the at least one sensor.

In one embodiment, the the system comprises at least one sensor for determining osmolarity or osmolality at a target site and wherein the system adjusts the first and second flow rates based on feedback from the at least one sensor.

In one embodiment, the system adjusts flow rate to maintain a desired osmolarity or osmolality at the target site.

In another aspect, a system coupled to a catheter and operable to provide a continuous delivery of contrast and of a hyperosmotic fluid supply is provided, the system includes a controller and computer memory having executable instructions stored thereon that when executed cause the controller to performing a method includes: injecting the contrast and determining a rate of flow that achieves angiographic filling of the target blood vessel at a first time; injecting the hyperosmotic fluid continuously at the rate of flow that achieves angiographic filling at the first time for a first period of time; injecting the contrast and determining a rate of flow that achieves angiographic filling of the target blood vessel at a second time following the first period of time; and injecting the hyperosmotic fluid continuously at the rate of flow that achieves angiographic filling at the second time for a second period of time.

In one embodiment, the hyperosmotic fluid comprises an osmotic embolic agent.

In one embodiment, the first and second periods of time are about 20 minutes to about 30 minutes.

In one embodiment, the method includes repeating the steps of injecting contrast and the hyperosmotic fluid until the flow rate at the second time signals completion of osmotic embolization at the target vessel.

In one embodiment, the system includes at least one sensor for determining flow rate and wherein the first and second flow rates are determined based on feedback from the sensor.

In one embodiment, the system includes at least one sensor for determining flow rate and wherein the first and second flow rates are determined based on feedback from the at least one sensor.

In one embodiment, the system includes at least one sensor for determining osmolarity or osmolality at a target site and wherein the system adjusts the first and second flow rates based on feedback from the at least one sensor.

In one embodiment, the system adjusts flow rate to maintain a desired osmolarity or osmolality at the target site.

BRIEF DESCRIPTION OF THE DRAWINGS

FIG. 3 is a chart comparing other embolization techniques with one or more embodiments of the osmotic embolization techniques disclosed herein.

DETAILED DESCRIPTION

The present application provides devices and methods for achieving or otherwise facilitating continuous or near continuous flow of osmotic embolic material or agents that overcome at least some of the shortcomings in the delivery processes and systems known the art. The application further provides methods and materials for the continuous, uninterrupted delivery of a fluid through a catheter for embolization so that appropriate flow rate can be determined and controlled by the operator of the system.

The devices/systems are illustrated in the figures of the accompanying drawings that are meant to be exemplary and not limiting, in which like references are intended to refer to like or corresponding parts and which all or some of the following components may or not be required. In certain embodiments, devices and methods are provided for the continuous, uninterrupted delivery of a fluid through a catheter for embolization, such that the appropriate flow rate can be determined and controlled by the operator and/or the system.

Figure 1:
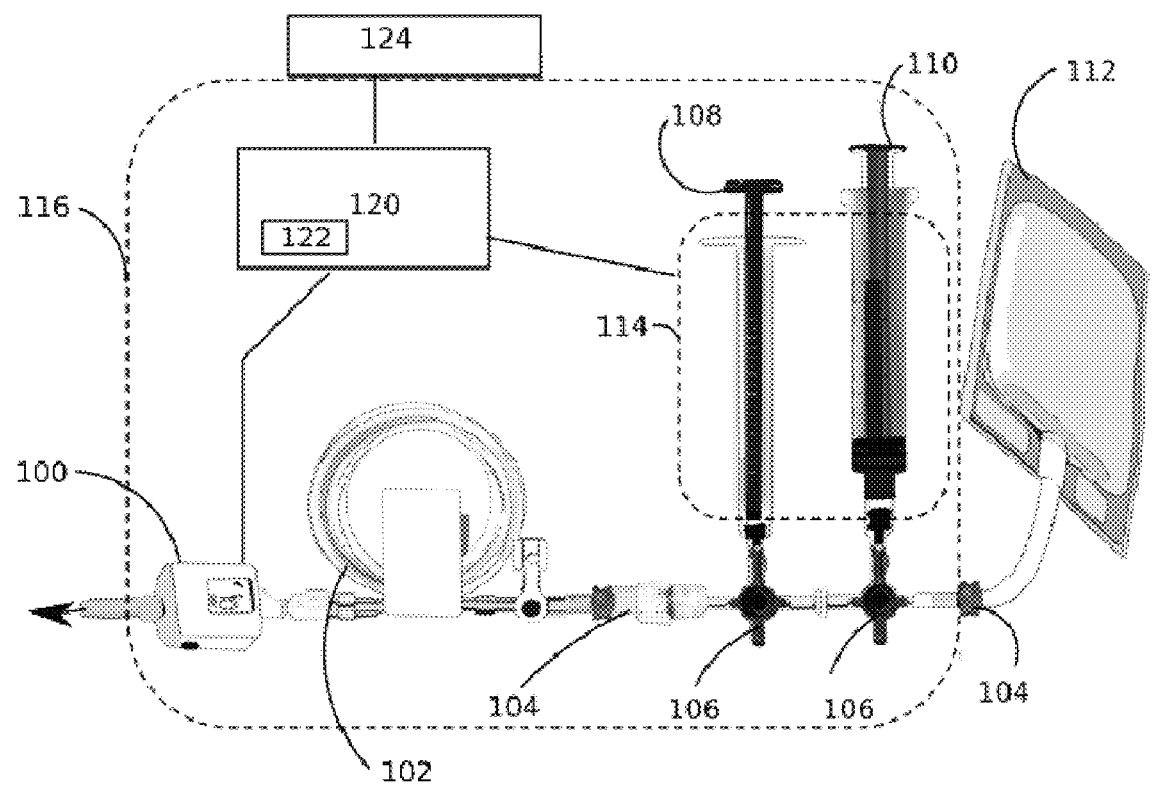
FIG. 1 is a view depicting an exemplary system or setup for osmotic embolization using a high-pressure syringe infusion device and intermittent angiographic confirmation of adequate flow.
Figure 2:
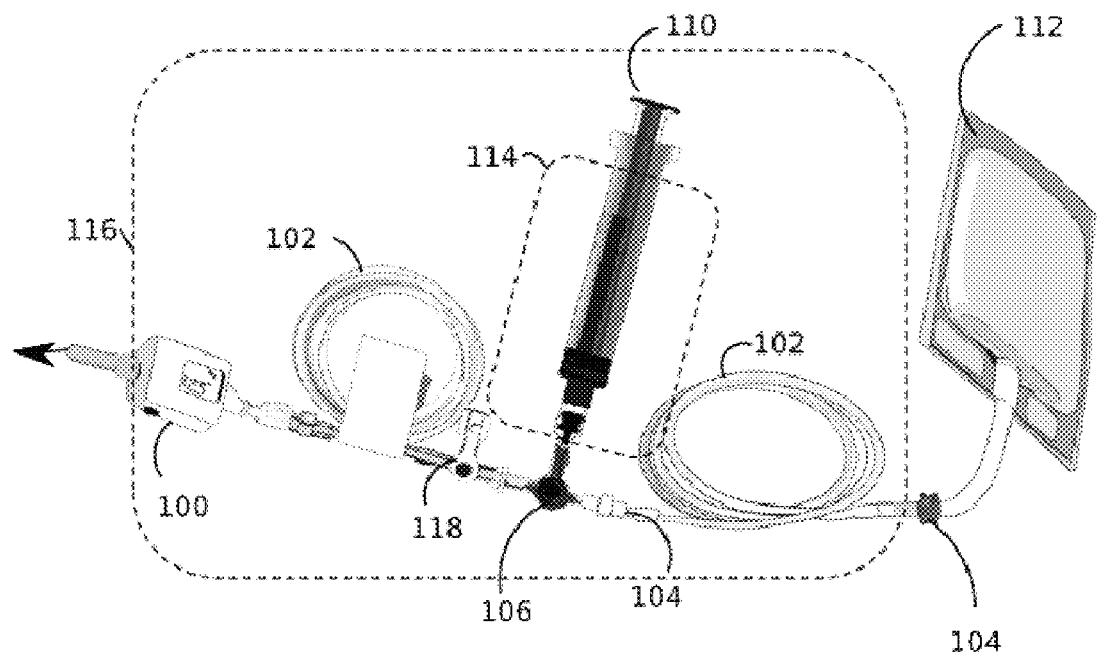
FIG. 2 is a view depicting an exemplary system or setup for osmotic embolization using a low or normal-pressure syringe infusion device and intermittent angiographic confirmation of adequate flow.

Referring to FIGS. 1-2, the devices/systems generally include one or more of the following components arranged in series as shown in the drawings: a pressure sensor or manometer 100, preferably an in-line high pressure manometer; tubing 102, preferably high pressure tubing; a check or one-way valve 104, preferably a high back pressure one way valve; an in-line flow valve 118; one or a plurality of 3-way stopcocks or valves 106; one or more syringes, pumps, or other sources of pressurized fluids, such as a 1 cc high pressure syringe(s) 108 and a 10 cc high pressure syringe 110 for contrast; and a source of pressurized osmotic embolic agent, such as a pump and/or reservoir 112 (bag and administration kit). Flow occurs in the system diagram from the reservoir 112 toward the pressure sensor, which exits toward the catheter.

Although the device/system is shown conceptually in FIGS. 1-2 as individual components, it is understood that the components may be housed in a single unit 116 with the appropriate inputs and outputs for automated operation of the process(es) disclosed herein. In this regard, the system may include a controller/processor 200 and computer memory 122 that stores executable instruction for controlling one or more of the components 100-118. The system may further include sensors 100, pumps 108, 110, and a display 124 that displays the operating parameters of the device, such as pressure measurements, flow rate, osmolarity, electrical conductance, etc., based on readings from the one or more sensors 100.

The device/system according to at least one embodiment allows the controlled continuous, high volume uninterrupted injection through a catheter into an arterial blood vessel with intermittent fluoroscopic visualization. This is done by the operator and/or the system by repeatedly injecting via the high-pressure syringe or pumps 108, 110 at the rate that contrast injected under fluoroscopy leads to complete opacification of the vessel with little reflux. Two embodiments are described that use a micro-catheter where high pressures for larger volumes are requires (FIG. 1) and a larger catheter where near physiological pressures can meet the requirements (FIG. 2).

In a third embodiment the task of the operator and visualization may be taken over by an algorithm-controlled pump/actuator and sensors within the catheter. The catheter may be similar to the catheter disclosed in U.S. Pat. No. 9,463,113, which is incorporate herein by reference. The pump/actuator and sensors may be configured to assure that the osmolarity/conductance of the infused agent at the distal vessel is close to the undiluted value of the embolic agent, and that there is no reflux. The sensors may take advantage of the differences in the osmolarity or electrical conductance of native blood vs the osmotic embolic agents. Blood osmolarity is in the range of 300 mOsm/L: Mannitol (20%) is 4 times greater and Hypertonic saline (3%) is 3 times greater. Interestingly 23% saline (26× greater) is routinely used in critical care. Sensors attuned to electrical conductance can also be used, as blood is a fair conductor, hypertonic saline an excellent conductor, and mannitol in distilled water a poor conductor.

Although methods and device may be described herein by way of example in relation to specific endovascular interventions or particular patient anatomy it is understood that the methods and devices of the present invention are equally applicable to interventions or anatomy not disclosed and therefore not limited thereto.

Referring to FIG. 1, when high pressures are needed to move the hyperosmotic emboli through a narrow and long catheter and completely replace the normal blood flow, the following embodiment is envisioned. After the catheter is placed in the target blood vessel, the device may be used to inject contrast at a rate that totally fills the target vessel (rate of complete opacification), this rate is noted. The stopcocks 106 may then be adjusted, and the flow rate passing through the system is continued by repeated injections of the self-filling syringe or continuous pump with the osmotic embolic agent from the reservoir 112. The valves 104 assure antegrade flows. The connecting tubing can act as a pressurized reservoir to smooth the flow when needed. Intermittently, the stopcock 106 can be turned to allow contrast to be be injected.

Referring to FIG. 2, when high pressures are not needed to move the hyperosmotic emboli through the catheter to completely replace the normal blood flow, the following embodiment may be used. After the catheter is placed in the target blood vessel, the device may be used to inject contrast at a rate that totally fills the target vessel, the rate is noted. The flow control valve 118 may be used to adjust the flow from the pressurized bag or pump 112 containing the osmotic embolic agent. The flow rate is monitored by repeated injections of contrast and the flow-valve 118 adjusted accordingly to maintain filling of the target vessel. The valves 104 assure antegrade flows. The connecting tubing can act as a pressurized reservoir to smooth the flow when needed. Intermittently the stopcock 106 can be turned, and contrast can be injected as discussed above.

The Method

Present methods may use the intermittent injection of embolic agents. In a few instances, slow continuous small injections have been used, but without the total or near total replacement of the native blood flow.

The method taught in this application is distinctly different than the prior art. As discussed herein, the method may include the following:

A catheter and/or microcatheter is placed in a blood vessel feeding the tumor.

Contrast is injected into the vessel and an angiogram obtained.

Normal tissue and dangerous collaterals are determined.

A transluminal Syringe (TLS) is loaded with the contrast and osmotic embolic agent, as described, with the osmotic agent being in the fluid bag and/or pump, care being taken to remove all air by injecting a number of times to clear any bubbles.

The method for micro-catheters requires high pressures (25-250 psi) to develop the flow through a relatively small and long catheter needed for filling the vessel. In FIG. 1, flow of contrast is turned on determine the flow rate necessary to fill the blood vessel. That is, stopcock 106 may be turned to the contrast ON position, [which in this device simultaneously turns the osmotic embolic flow OFF]. The TL syringe is then withdrawn, which draws contrast from the contrast reserve. Next, under fluoroscopy, the TL syringe injects its contents and the rate of the injection is adjusted by the operator or by the system to fully fill the blood vessel angiographically, allowing some slight reflux. This maneuver is repeated/adjusted under fluoroscopy until the operator can perform the maneuver constantly and note this flow rate. Alternatively, the system can adjust the flow rate of contrast until the desired rate for angiographic filling of the vessel is achieved. At this point, the stopcock 106 is turned to the ON position allowing the osmotic embolic agent to flow [which turns OFF the contrast supply] and the noted rate of contrast injection and withdrawal or is continued with the osmotic embolic agent. After 20-30 seconds of injection of osmotic embolic agent, the angiographic filling flow rate may be retested. That is, three-way stopcocks may again be changed to allow the contrast to be injected and the osmotic agent shut off. This is done under fluoroscopy. Again, the rate is noted, and the stopcocks changed again to stop contrast and to deliver the osmotic material at the new rate noted. This sequence it repeated until the effect of the osmotic embolization material has killed the target tissue and the flow becomes nearly stagnant.

The method for regular sized catheters that do not require high pressures and the user/system can use a pressure bag or similar device to create pressure adequate to fill the target vessel. In this situation the operator uses the flow valve to control the osmotic embolic agent and contrast flow. The valve 118 is used to have the flow adequate to entirely fill the blood vessel, tolerating a small amount of reflux seen at pressures and flows of the diastole's nadir. Additionally, in this and the prior description a controller and pressure or volume pump could be used to control/set the injection rate.

The method for a sensor embedded (or separate) catheter with automated algorithm-controlled pump system requires that the catheter is placed in the target vessel described above. Under fluoroscopic control the distal sensor (on or separate from the catheter) that measures osmolarity or an osmolarity marker, is placed distal to the infusion in the target vessel. The proximal sensor (if used in this embodiment) is placed in the feeding vessel, just proximal to the point of potential reflux. The algorithm will preferably control the pump to keep the distal sensor at an osmotic marker's value much higher than blood (3-4×), slow the infusion down, if the proximal sensor reads too high for the situation allowing reflux: Range; ([Blood Osmolarity]×[1.2 to 1.5]). Confirmation of flow is done intermittently by injection of contrast with fluoroscopy, that continues the flow at the given rate and simultaneously disables the sensors. The connecting tubing acts as a reservoir.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. An endovascular interventional method comprising:
   inserting a catheter into a target blood vessel, wherein the catheter is coupled to a controller and one or more sensors, the controller and the one more sensors providing a continuous delivery of contrast and of a hyperosmotic fluid supply;
   injecting the contrast and determining a rate of flow that achieves angiographic filling of the target blood vessel at a first time;
   injecting the hyperosmotic fluid continuously at the rate of flow that achieves angiographic filling at the first time for a first period of time;
   injecting the contrast and determining a rate of flow that achieves angiographic filling of the target blood vessel at a second time following the first period of time;
   injecting the hyperosmotic fluid continuously at the rate of flow that achieves angiographic filling at the second time for a second period of time;
   injecting the contrast and determining a rate of flow that achieves complete opacification of the target blood vessel; and
   injecting the hyperosmotic fluid continuously until dehydration of the target blood vessel occurs.

2. The method of claim 1, wherein the hyperosmotic fluid comprises an osmotic embolic agent.

3. The method of claim 1, wherein the first period of time is about 20 minutes to about 30 minutes.

4. The method of claim 1, wherein the second period of time is about 20 minutes to about 30 minutes.

5. The method of claim 1, comprising repeating the steps of injecting contrast and the hyperosmotic fluid until the flow rate at the second time is reduced.

6. The method of claim 1, comprising repeating the steps of injecting contrast and the hyperosmotic fluid until the flow rate at the second time is reduced to a negligible flow rate.

7. The method of claim 1, comprising repeating the steps of injecting contrast and the hyperosmotic fluid until the flow rate at the second time signals completion of osmotic embolization at the target vessel.

8. The method of claim 1, wherein flow of the contrast is off when flow of the hyperosmotic fluid is turned on.

9. The method of claim 1, wherein flow of the hyperosmotic fluid is off when flow of the contrast is turned on.

10. The method of claim 1, wherein the one or more sensors comprises at least one flow rate sensor for determining flow rate and wherein the first and second flow rates are determined based on feedback from the at least one flow rate sensor.

11. The method of claim 1, wherein the one or more sensors comprises at least one osmolarity sensor for determining osmolarity or osmolality at a target site and wherein the system adjusts the first and second flow rates based on feedback from the at least one osmolarity sensor.

12. The method of claim 11, wherein the controller adjusts flow rate to maintain a desired osmolarity or osmolality at the target site.

13. A system coupled to a catheter and operable to provide a continuous delivery of contrast and of a hyperosmotic fluid supply, the system comprising a controller, the controller and one or more sensors configured to perform:
   injecting the contrast and determining a rate of flow that achieves angiographic filling of the target blood vessel at a first time;
   injecting the hyperosmotic fluid continuously at the rate of flow that achieves angiographic filling at the first time for a first period of time;
   injecting the contrast and determining a rate of flow that achieves angiographic filling of the target blood vessel at a second time following the first period of time;
   injecting the hyperosmotic fluid continuously at the rate of flow that achieves angiographic filling at the second time for a second period of time;
   injecting the contrast and determining a rate of flow that achieves complete opacification of the target blood vessel; and
   injecting the hyperosmotic fluid continuously until dehydration of the target blood vessel occurs.

14. The system of claim 13, wherein the hyperosmotic fluid comprises an osmotic embolic agent.

15. The system of claim 13, wherein the first and second periods of time are about 20 minutes to about 30 minutes.

16. The system of claim 13, the controller further configured to perform: repeating the steps of injecting contrast and the hyperosmotic fluid until the flow rate at the second time signals completion of osmotic embolization at the target vessel.

17. The system of claim 16, comprising at least one flow rate sensor for determining flow rate and wherein the first and second flow rates are determined based on feedback from the flow rate sensor.

18. The system of claim 13, wherein controller is controlled by an algorithm.

19. The system of claim 13, comprising at least one osmolarity sensor for determining osmolarity or osmolality at a target site and wherein the system adjusts the first and second flow rates based on feedback from the at least one osmolarity sensor.

20. The system of claim 19, wherein the system adjusts flow rate to maintain a desired osmolarity or osmolality at the target site.

* * * * *